United States Patent
Shih et al.

(10) Patent No.: US 9,987,417 B2
(45) Date of Patent: Jun. 5, 2018

(54) IMPLANTABLE DRUG-DELIVERY DEVICES, AND APPARATUS AND METHODS FOR FILLING THE DEVICES

(71) Applicants: Jason Shih, Yorba Linda, CA (US);
Yu-Chong Tai, Pasadena, CA (US);
Changlin Pang, Pasadena, CA (US);
Sean Caffey, Hawthrone, CA (US);
Raymond Peck, Los Angeles, CA (US);
Fukang Jiang, Pasadena, CA (US);
Mark Humayun, Glendale, CA (US)

(72) Inventors: Jason Shih, Yorba Linda, CA (US);
Yu-Chong Tai, Pasadena, CA (US);
Changlin Pang, Pasadena, CA (US);
Sean Caffey, Hawthrone, CA (US);
Raymond Peck, Los Angeles, CA (US);
Fukang Jiang, Pasadena, CA (US);
Mark Humayun, Glendale, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 220 days.

(21) Appl. No.: 14/706,498

(22) Filed: May 7, 2015

(65) Prior Publication Data
US 2015/0314064 A1    Nov. 5, 2015

Related U.S. Application Data

(62) Division of application No. 13/709,301, filed on Dec. 10, 2012, now Pat. No. 9,050,407, which is a division
(Continued)

(51) Int. Cl.
*A61M 1/00* (2006.01)
*A61M 5/142* (2006.01)
(Continued)

(52) U.S. Cl.
CPC ....... *A61M 5/14212* (2013.01); *A61F 9/0017* (2013.01); *A61M 5/14276* (2013.01);
(Continued)

(58) Field of Classification Search
CPC ........ A61M 5/14276; A61M 2209/045; A61M 39/0208; A61M 39/04; A61M 2005/1403; A61M 5/204; A61M 2005/3114
See application file for complete search history.

(56) References Cited

U.S. PATENT DOCUMENTS

| 3,731,681 A | 5/1973 | Blackshear et al. |
| 3,916,899 A | 11/1975 | Theeuwes et al. |

(Continued)

FOREIGN PATENT DOCUMENTS

| CA | 946696 A1 | 5/1974 |
| CH | 570169 A5 | 12/1975 |

(Continued)

OTHER PUBLICATIONS

"Krupin Eye Valve with Scleral Buckle, Krupin Eye Valve With Disk", Hood Laboratories Catalogue, F 079 Rev., Nov. 1992, 4 pages.
(Continued)

*Primary Examiner* — Rebecca E Eisenberg
(74) *Attorney, Agent, or Firm* — Morgan, Lewis & Bockius LLP

(57) ABSTRACT

In various embodiments, a tool is employed in filling a drug-delivery device. The tool may include, for example, a needle that is admitted through a fill port of the drug-delivery device.

8 Claims, 11 Drawing Sheets

Related U.S. Application Data of application No. 12/463,247, filed on May 8, 2009, now Pat. No. 8,348,897.

(60) Provisional application No. 61/051,422, filed on May 8, 2008, provisional application No. 61/197,752, filed on Oct. 30, 2008, provisional application No. 61/197,817, filed on Oct. 30, 2008, provisional application No. 61/198,126, filed on Nov. 3, 2008.

(51) Int. Cl.
| | | |
|---|---|---|
| *A61F 9/00* | (2006.01) | |
| *A61M 39/02* | (2006.01) | |
| *A61M 5/36* | (2006.01) | |
| A61M 5/14 | (2006.01) | |
| A61M 5/148 | (2006.01) | |
| A61M 5/168 | (2006.01) | |
| A61M 39/00 | (2006.01) | |

(52) U.S. Cl.
CPC .......... *A61M 5/36* (2013.01); *A61M 39/0208* (2013.01); *A61M 5/148* (2013.01); *A61M 5/16881* (2013.01); *A61M 2005/1403* (2013.01); *A61M 2039/0072* (2013.01); *A61M 2039/0081* (2013.01); *A61M 2039/0235* (2013.01); *A61M 2209/045* (2013.01)

(56) References Cited

U.S. PATENT DOCUMENTS

| | | |
|---|---|---|
| 3,977,404 A | 8/1976 | Theeuwes |
| 4,150,673 A | 4/1979 | Watt |
| 4,164,560 A | 8/1979 | Folkman et al. |
| 4,543,088 A | 9/1985 | Boatman et al. |
| 4,553,973 A | 11/1985 | Edgren |
| 4,573,994 A | 3/1986 | Fischell et al. |
| 4,673,394 A | 6/1987 | Fenton, Jr. et al. |
| 4,738,657 A | 4/1988 | Hancock et al. |
| 4,751,926 A | 6/1988 | Sasaki |
| 4,760,837 A | 8/1988 | Petit |
| 4,781,675 A | 11/1988 | White |
| 4,781,695 A | 11/1988 | Dalton |
| 4,804,054 A | 2/1989 | Howson et al. |
| 4,838,887 A | 6/1989 | Idriss |
| 4,853,224 A | 8/1989 | Wong |
| 4,888,176 A | 12/1989 | Langer et al. |
| 4,955,861 A | 9/1990 | Enegren et al. |
| 4,959,217 A | 9/1990 | Sanders et al. |
| 5,007,647 A | 4/1991 | Gulick |
| 5,135,499 A | 8/1992 | Tafani et al. |
| 5,147,647 A | 9/1992 | Darougar |
| 5,164,188 A | 11/1992 | Wong |
| 5,171,213 A | 12/1992 | Price, Jr. |
| 5,178,604 A | 1/1993 | Baerveldt et al. |
| 5,201,715 A | 4/1993 | Masters |
| 5,252,192 A | 10/1993 | Ludwig |
| 5,312,357 A | 5/1994 | Buijs et al. |
| 5,389,077 A | 2/1995 | Melinyshyn et al. |
| 5,407,441 A | 4/1995 | Greenbaum |
| 5,443,505 A | 8/1995 | Wong et al. |
| 5,462,739 A | 10/1995 | Dan et al. |
| 5,472,436 A | 12/1995 | Fremstad |
| 5,476,445 A | 12/1995 | Baerveldt et al. |
| 5,478,328 A | 12/1995 | Silverman et al. |
| 5,704,520 A | 1/1998 | Gross |
| 5,725,017 A | 3/1998 | Elsberry et al. |
| 5,725,493 A | 3/1998 | Avery et al. |
| 5,798,115 A | 8/1998 | Santerre et al. |
| 5,824,072 A | 10/1998 | Wong |
| 5,830,173 A | 11/1998 | Avery et al. |
| 5,836,935 A | 11/1998 | Ashton et al. |
| 5,868,697 A | 2/1999 | Richter et al. |
| 5,904,144 A | 5/1999 | Hammang et al. |
| 5,989,579 A | 11/1999 | Darougar et al. |
| 6,144,106 A | 11/2000 | Bearinger et al. |
| 6,251,090 B1 | 6/2001 | Avery et al. |
| 6,264,971 B1 | 7/2001 | Darougar et al. |
| 6,281,192 B1 | 8/2001 | Leahy et al. |
| 6,375,972 B1 | 4/2002 | Guo et al. |
| 6,416,777 B1 | 7/2002 | Yaacobi |
| 6,478,783 B1 | 11/2002 | Moorehead |
| 6,519,569 B1 | 2/2003 | White et al. |
| 6,520,936 B1 | 2/2003 | Mann |
| 6,527,744 B1 | 3/2003 | Kriesel et al. |
| 6,537,268 B1 | 3/2003 | Gibson et al. |
| 6,564,087 B1 | 5/2003 | Pitris et al. |
| 6,669,950 B2 | 12/2003 | Yaacobi |
| 6,713,081 B2 | 3/2004 | Robinson et al. |
| 6,719,750 B2 | 4/2004 | Varner et al. |
| 6,852,106 B2 | 2/2005 | Watson et al. |
| 6,962,580 B2 | 11/2005 | Adams et al. |
| 6,976,974 B2 | 12/2005 | Houde et al. |
| 7,070,577 B1 | 7/2006 | Haller et al. |
| 7,191,011 B2 | 3/2007 | Cantlon |
| 7,276,050 B2 | 10/2007 | Franklin |
| 7,637,897 B2 | 12/2009 | Ginggen |
| 8,025,639 B2 | 9/2011 | Powers et al. |
| 8,177,762 B2 | 5/2012 | Beasley et al. |
| 8,202,259 B2 | 6/2012 | Evans et al. |
| 8,348,897 B2 | 1/2013 | Shih et al. |
| 2002/0040208 A1 | 4/2002 | Flaherty et al. |
| 2002/0103412 A1 | 8/2002 | Trimmer |
| 2002/0128604 A1 | 9/2002 | Nakajima |
| 2002/0188282 A1 | 12/2002 | Greenberg |
| 2003/0014036 A1 | 1/2003 | Varner et al. |
| 2003/0064088 A1 | 4/2003 | Carvalho et al. |
| 2003/0069560 A1 | 4/2003 | Adamis et al. |
| 2003/0078195 A1 | 4/2003 | Kristensen et al. |
| 2003/0141618 A1 | 7/2003 | Braithwaite et al. |
| 2004/0028655 A1 | 2/2004 | Nelson et al. |
| 2004/0143221 A1 | 7/2004 | Shadduck |
| 2004/0199130 A1 | 10/2004 | Chornenky et al. |
| 2005/0175708 A1 | 8/2005 | Carrasquillo et al. |
| 2005/0187515 A1 | 8/2005 | Varrichio et al. |
| 2005/0208103 A1 | 9/2005 | Adamis et al. |
| 2006/0089619 A1 | 4/2006 | Ginggen |
| 2006/0167435 A1 | 7/2006 | Adamis et al. |
| 2006/0235428 A1 | 10/2006 | Silvestrini |
| 2006/0258994 A1 | 11/2006 | Avery |
| 2006/0259015 A1 | 11/2006 | Steinbach |
| 2006/0264897 A1 | 11/2006 | Lobl et al. |
| 2007/0021735 A1 | 1/2007 | Bhavaraju et al. |
| 2007/0078391 A1 | 4/2007 | Wortley et al. |
| 2007/0112328 A1 | 5/2007 | Steinbach et al. |
| 2007/0255235 A1 | 11/2007 | Olsen et al. |
| 2007/0255261 A1 | 11/2007 | Haase |
| 2008/0039792 A1 | 2/2008 | Meng et al. |
| 2008/0045930 A1 | 2/2008 | Makin et al. |
| 2008/0181930 A1 | 7/2008 | Rodstrom et al. |
| 2008/0234637 A1 | 9/2008 | McConnell et al. |
| 2009/0028824 A1 | 1/2009 | Chiang et al. |
| 2009/0088732 A1 | 4/2009 | Villegas |
| 2009/0118683 A1 | 5/2009 | Hanson et al. |
| 2009/0192493 A1 | 7/2009 | Meng et al. |
| 2009/0227855 A1 | 9/2009 | Hill et al. |
| 2009/0240241 A1 | 9/2009 | Hyde et al. |
| 2009/0306595 A1 | 12/2009 | Shih et al. |
| 2009/0311133 A1 | 12/2009 | Pang et al. |
| 2010/0004639 A1 | 1/2010 | Pang et al. |
| 2010/0277316 A1 | 11/2010 | Schlangen et al. |
| 2012/0234433 A1 | 9/2012 | Shih et al. |
| 2013/0102962 A1 | 4/2013 | Shih et al. |
| 2013/0116664 A1 | 5/2013 | Tai et al. |
| 2013/0116665 A1 | 5/2013 | Humayun et al. |
| 2013/0116666 A1 | 5/2013 | Shih et al. |
| 2013/0226105 A1 | 8/2013 | Hyde et al. |
| 2013/0289482 A1 | 10/2013 | Meng et al. |

FOREIGN PATENT DOCUMENTS

| | | |
|---|---|---|
| CN | 1321096 A | 11/2001 |
| CN | 103349803 A | 10/2013 |

(56) References Cited

FOREIGN PATENT DOCUMENTS

| | | |
|---|---|---|
| CN | 103394142 A | 11/2013 |
| CN | 103608054 A | 2/2014 |
| DE | 3915708 A1 | 2/1990 |
| DE | 3390255 C2 | 6/1992 |
| DE | 4436540 A1 | 4/1996 |
| DE | 202004008151 U1 | 11/2005 |
| EP | 0251680 A2 | 1/1988 |
| EP | 0646381 A1 | 4/1995 |
| EP | 1649884 A1 | 4/2006 |
| EP | 2686038 A1 | 1/2014 |
| EP | 2727616 A1 | 5/2014 |
| EP | 2760504 A2 | 8/2014 |
| FR | 2091189 A5 | 1/1972 |
| GB | 1345764 A | 2/1974 |
| IE | 38474 B1 | 3/1978 |
| JP | 2-191468 A | 7/1990 |
| JP | 2002-529185 A | 9/2002 |
| JP | 3503852 B2 | 3/2004 |
| JP | 2004-535886 A | 12/2004 |
| JP | 2005-131414 A | 5/2005 |
| JP | 2005-521433 A | 7/2005 |
| JP | 2006-501014 A | 1/2006 |
| JP | 2006-526430 A | 11/2006 |
| JP | 2011-509120 A | 3/2011 |
| JP | 2014-28145 A | 2/2014 |
| WO | 8401718 A1 | 5/1984 |
| WO | 1995/013838 A1 | 5/1995 |
| WO | 1999/017749 A1 | 4/1999 |
| WO | 1999/038552 A1 | 8/1999 |
| WO | 1999/062576 A1 | 12/1999 |
| WO | 20001026367 A2 | 5/2000 |
| WO | 2000/040089 A1 | 7/2000 |
| WO | 2000/074751 A1 | 12/2000 |
| WO | 2001/012158 A1 | 2/2001 |
| WO | 2001/056634 A1 | 8/2001 |
| WO | 2001/066173 A1 | 9/2001 |
| WO | 2001/094784 A1 | 12/2001 |
| WO | 2002/040208 A1 | 5/2002 |
| WO | 2003/002170 A2 | 1/2003 |
| WO | 2003/009774 A2 | 2/2003 |
| WO | 2003/009784 A1 | 2/2003 |
| WO | 2003/024360 A1 | 3/2003 |
| WO | 2004/014969 A1 | 2/2004 |
| WO | 2004/066871 A2 | 8/2004 |
| WO | 2004/073551 A2 | 9/2004 |
| WO | 2004/073765 A2 | 9/2004 |
| WO | 2005/046769 A2 | 5/2005 |
| WO | 2006/012280 A1 | 2/2006 |
| WO | 2006/014793 A1 | 2/2006 |
| WO | 2006/075016 A1 | 7/2006 |
| WO | 2006/096686 A1 | 9/2006 |
| WO | 2006/114638 A2 | 11/2006 |
| WO | 2007/084765 A2 | 7/2007 |
| WO | 2007/106557 A2 | 9/2007 |
| WO | 2009/137777 A2 | 11/2009 |
| WO | 2011/022484 A1 | 2/2011 |
| WO | 2012/125695 A1 | 9/2012 |
| WO | 2013/052414 A2 | 4/2013 |
| WO | 2013/052414 A3 | 6/2013 |

OTHER PUBLICATIONS

"The Optimed Advantage", Regulated Drainage with No Moving Parts, Journal of Glaucoma, vol. 2, No. 3, 1993, 7 pages.
Examination Report Received for European Patent Application No. 09701298.3, dated Jan. 29, 2013, 5 pages.
Examination Report Received for European Patent Application No. 09743763.6, dated Feb. 6, 2015, 4 pages.
Examination Report Received for European Patent Application No. 10008072.0, dated Jun. 17, 2013, 6 pages.
Examination Report Received for Australian Patent Application No. 2012230033, dated Jul. 9, 2014, 4 pages.
Chen et al., "Floating-Disk Parylene Micro Check Valve", Micro Electro Mechanical Systems, MEMS IEEE 20th International Conference, Jan. 21-25, 2007, pp. 453-456.
Chen et al., "Floating-Disk Parylene Microvalve for Self-Regulating Biomedical Flow Controls", Micro Electro Mechanical Systems, MEMS, IEEE 21st International Conference, Jan. 13-17, 2008, pp. 575-578.
Chen et al., "Surface-Micromachined Parylene Dual Valves for On-Chip Unpowered Microflow Regulation", Journal of Microelectromechanical Systems, vol. 16, No. 2, Apr. 2007, pp. 223-231.
Choudhri et al., "A Comparison of Dorzolamide-Timolol Combination Versus The Concomitant Drugs.", American Journal of Ophthalmology, vol. 130, No. 6, Dec. 2000, pp. 832-833.
Examination Report Received for Chinese Patent Application No. 201310157066.7 dated Oct. 29, 2014, 10 pages (4 pages of English Translation & 6 pages of Official copy).
Examination Report Received for Chinese Patent Application No. 201280013608.7 dated Dec. 17, 2014, 16 pages (8 pages of English Translation & 8 pages of Official copy).
Durham, N.C., "FDA Approves an Industry FIRST—The MED-EL Cochlear Implant System is FDA Approved for Use with Magnetic Resonance Imaging (MRI)", PR Newswire, Jun. 18, 2003, 3 pages.
Eliason et al., "An Ocular Perfusion System", Investigate Ophthalmology Visual Science, vol. 19, No. 1, Jan. 1980, pp. 102-105.
Examination Report Received for European Patent Application No. 07753177.0, dated Jan. 29, 2009, 6 pages.
Examination Report Received for European Patent Application No. 07753177.0, dated Feb. 5, 2010, 3 pages.
Xie et al., "An Electrochemical Pumping System for On-Chip Gradient Generation", Analytical Chemistry, vol. 74, No. 13, May 2004, 8 pages.
European Search Report received for European Patent Application No. 10008072.0, dated Mar. 1, 2011, 11 pages.
Examination Report Received for European Patent Application No. 09743763.6, dated Sep. 9, 2014, 3 pages.
Extended European Search Report received for European Patent Application No. 14152346.4, dated Apr. 9, 2014, 6 pages.
Hashizoe et al., "Scleral Plug of Biodegradable Polymers for Controlled Drug Release in the Vitreous", Arch Ophthalmology, vol. 112, No. 10, Oct. 1994, pp. 1380-1384.
Jabs, Douglas A., "Treatment of Cytomegalovirus Retinitis—1992", Arch Ophthalmology, vol. 110, No. 2, Feb. 1992, pp. 185-187.
Examination Report Received for Japanese Patent Application No. 2013-157652, dated Jul. 29, 2014, 3 pages. (Official Copy Only).
Examination Report Received for Japanese Patent Application No. 2013-243564, dated Sep. 18, 2014, 7 pages (4 pages of English Translation and 3 pages of Official copy).
Khouri et al., "Use of Fixed-Dose Combination Drugs for the Treatment of Glaucoma", Drugs Aging, vol. 24, No. 12, Dec. 2007, pp. 1007-1016.
Kimura et al., "A New Vitreal Drug Delivery System Using an Implantable Biodegradable Polymeric Device", Investigative Ophthalmology & Visual Science, vol. 35, No. 6, May 1994, pp. 2815-2819.
Lo et al., "A Refillable Polymer Drug Delivery Device for Treatment of Ocular Diseases", The Royal Society of Chemistry, Jan. 1, 2007, 28 pages.
Michelson et al., "Experimental Endophtalmitis Treated with an Implantable Osmotic Minipump", Arch. Ophthalmology, vol. 97, Jul. 1979, p. 1345.
Miki et al., "A Method for Chronic Drug Infusion Into the Eye", Japanese Journal of Ophthalmology, vol. 28, No. 2, 1984, pp. 140-146.
Examination Report Received for Mexican Patent Application No. MX/1/2010/012212, dated Mar. 3, 2014, 3 pages.
Examination Report Received for Mexican Patent Application No. MX/A/2010/007382, dated Sep. 30, 2013, 4 pages.
Examination Report Received for Mexican Patent Application No. MX/A/2010/007382, dated May 30, 2014, 3 pages.
PCT International Patent Application No. PCT/US2007/006530, International Search Report and Written Opinion dated Nov. 12, 2007, 15 pages.

(56) References Cited

OTHER PUBLICATIONS

PCT International Patent Application No. PCT/US2007/006530, Invitation to Pay Additional Fees and Partial International Search, dated Jul. 31, 2007, 7 pages.

PCT International Patent Application No. PCT/US2008/087690, International Search Report and Written Opinion dated Aug. 11, 2009, 15 pages.

PCT International Patent Application No. PCT/US2008/087690, Invitation to Pay Additional Fees and Partial International Search, dated May 15, 2009, 5 pages.

PCT International Patent Application No. PCT/US2009/030019, International Search Report and Written Opinion dated Jul. 20, 2009, 16 pages.

PCT International Patent Application No. PCT/US2009/030019, Invitation to Pay Additional Fees and Partial International Search, date May 6, 2009, 5 pages.

PCT International Patent Application No. PCT/US2009/043313, International Search Report and Written Opinion dated Feb. 25, 2010, 16 pages.

PCT International Patent Application No. PCT/US2009/043313, Invitation to Pay Additional Fees and Partial International Search, dated Nov. 16, 2009, 6 pages.

PCT International Patent Application No. PCT/US2009/043317, International Search Report and Written Opinion dated Feb. 16, 2010, 15 pages.

PCT International Patent Application No. PCT/US2009/043317, Invitation to Pay Additional Fees and Partial International Search, dated Nov. 16, 2009, 5 pages.

PCT International Patent Application No. PCT/US2009/043325, International Search Report and Written Opinion dated Nov. 12, 2009, 18 pages.

PCT International Patent Application No. PCT/US2012/029029, International Preliminary Report on Patentability dated Sep. 26, 2013, 9 pages.

PCT International Patent Application No. PCT/US2012/029029, International Search Report and Written Opinion dated Jul. 26, 2012, 13 pages.

PCT International Patent Application No. PCT/US2012/058286, International Search Report dated Apr. 5, 2013, 5 pages.

Pincus et al., "Why are Only 50% of Courses of Anti-Tumor Necrosis Factor Agents Continued for Only 2 Years in Some Settings? Need for Longterm Observations in Standard Care to Compliment Clinical Trials", The Journal of Reumatology, vol. 33, No. 12, Dec. 2006, pp. 2372-2375.

Pope et al., "MRI in Patients with High-Grade Gliomas Treated with Bevacizumab and Chemotherapy", Neurology, vol. 66, No. 8, Apr. 2006, pp. 1258-1260.

Rubsamen et al., "Prevention of Experimental Proliferative Vitreoretinopathy With a Biodegradable Intravitreal Implant for the Sustained Release of Fluorouracil", Arch. Ophthalmology, vol. 112, No. 3, Mar. 1994, pp. 407-413.

Sanborn et al., "Sustained-Release Ganciclovir Therapy for Treatment of Cytomegalovirus Retinitis", Arch. Ophthalmology, vol. 110, No. 2, Feb. 1992, pp. 188-195.

Smith et al., "Intravitreal Sustained-Release Ganiclovir", Arch Ophthlmology, vol. 110, No. 2, Feb. 1992, pp. 255-258.

Stark-Vance, "Bevacizumab and CPT-11 in the Treatment of Relapsed Malignant Glioma", Neuro Oncology, Abstract from the World Federation of Neuro-Oncology Second Quadrennial Meeting and Sixth Meeting of the European Association for Neuro-Oncology, vol. 7, No. 3, May 5-8, 2005, Jul. 2005, p. 369.

Steyer, Robert, "Alcon Eye-Drug Setback Raises the Stakes", Available online at <http://www.thestreet.comstory/10187873/1/alcon-eye-drug-setback-raises-the-stakes.html>, Oct. 14, 2004, 4 pages.

Strohmaier et al., "The Efficacy and Safety of the Dorzolamide-Timolol Combination Versus the Concomitant Administration of its Components.", Ophthalmology, vol. 105, No. 10, Oct. 1998, pp. 1936-1944.

PCT International Patent Application No. PCT/US2012/58286, International Preliminary Report on Patentability dated Apr. 10, 2014, 10 pages.

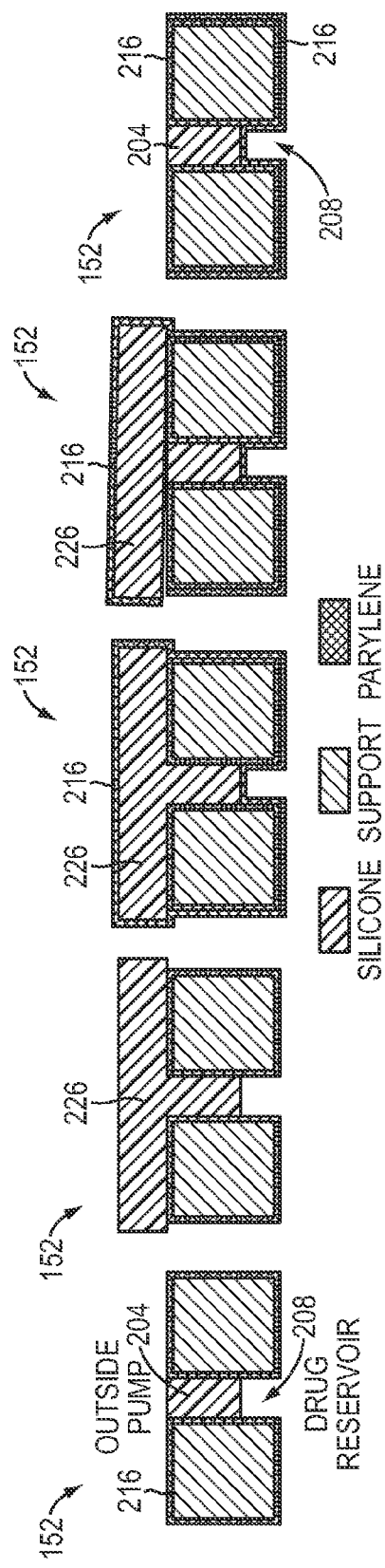

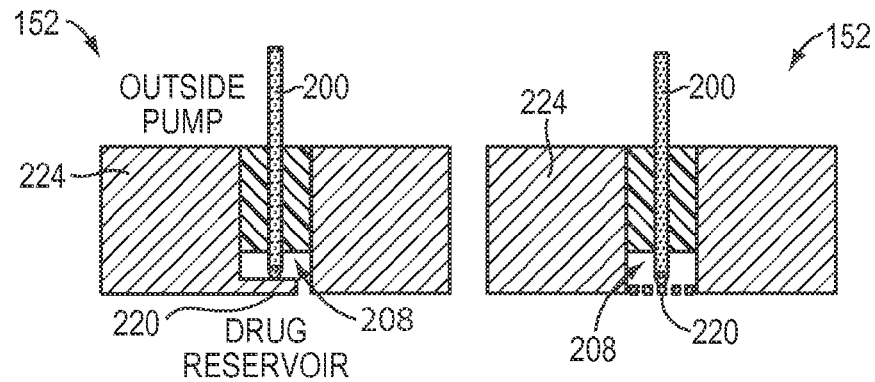
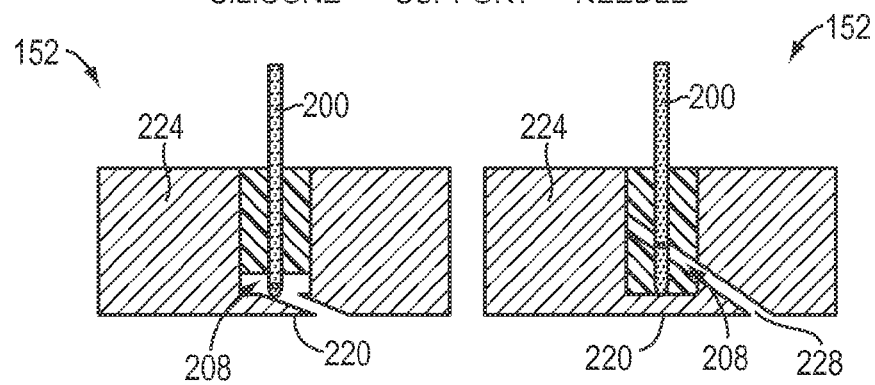
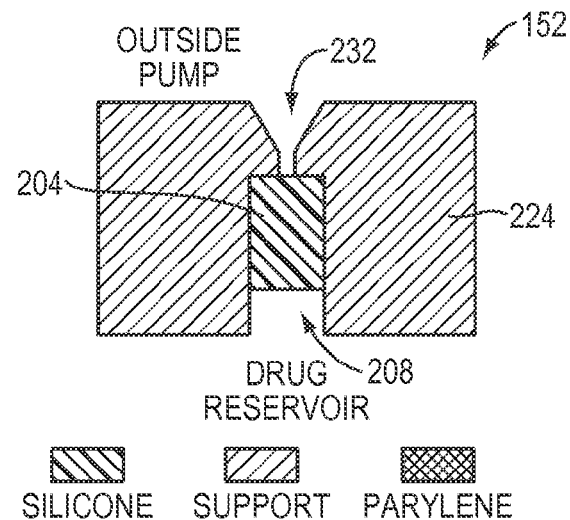

IMPLANTABLE DRUG-DELIVERY DEVICES, AND APPARATUS AND METHODS FOR FILLING THE DEVICES

CROSS-REFERENCE TO RELATED APPLICATIONS

This application is a divisional application of U.S. patent application Ser. No. 13/709,301, filed on Dec. 10, 2012, and a divisional application of U.S. patent Ser. No. 12/463,247, filed on May 8, 2009, which claims priority to and the benefit of, and incorporates herein by reference in their entireties, U.S. Provisional Patent Application Nos. 61/051,422, which was filed on May 8, 2008; 61/197,752, which was filed on Oct. 30, 2008; 61/197,817, which was filed on Oct. 30, 2008; and 61/198,126, which was filed on Nov. 3, 2008. The forgoing applications are incorporated herein by reference in their entireties.

TECHNICAL FIELD

In various embodiments, the invention relates to implantable drug-delivery devices and to apparatus and methods for filling such devices.

BACKGROUND

Medical treatment often requires the administration of a therapeutic agent (e.g., medicament, drugs, etc.) to a particular part of a patient's body. As patients live longer and are diagnosed with chronic and/or debilitating ailments, the likely result will be an increased need to place even more protein therapeutics, small-molecule drugs, and other medications into targeted areas throughout the patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted (and generally offer limited ability to change the dose in response to the clinical picture).

Another example is cancer, such as breast cancer or meningiomas, where large doses of highly toxic chemotherapies, such as rapamycin, bevacizumab (e.g., AVASTIN), or irinotecan (CPT-11), are typically administered to the patient intravenously, which may result in numerous undesired side effects outside the targeted area. Yet another example is drug delivery to the knee, where drugs often have difficulty penetrating the avascular cartilage tissue for diseases such as osteoarthritis.

Implantable drug-delivery devices, which may have a refillable drug reservoir, a cannula for delivering the drug, etc., generally allow for controlled delivery of pharmaceutical solutions to a specified target. As drug within the drug reservoir depletes, the physician can refill the reservoir with, for example, a syringe, while leaving the device implanted within the patient's body. This approach can minimize the surgical incision needed for implantation and typically avoids future or repeated invasive surgery or procedures.

A variety of challenges, however, are associated with refillable drug-delivery devices. For example, while a fill port may be located on a surface of the device to facilitate post-implantation access, the fact that the device is installed within the patient's anatomy may make such access uncomfortable for the patient and risk damage to the device. Such difficulties are especially problematic if the device is refilled manually. When filling the drug reservoir using a handheld syringe, for example, it is possible to generate large pressures in the syringe, particularly when small volumes are involved and the syringe plunger is of small diameter. These high pressures may damage the device and/or cause improper drug expulsion. Also, trying to refill the drug-delivery device with a handheld single-barrel syringe can require several cycles of needle insertion and withdrawal as different fluids are removed and injected into the device. This may cause stress for both the patient and the doctor, and creates unnecessary wear on the fill port.

A need exists, therefore, for improved implantable drug-delivery devices, and apparatus and methods for filling such devices.

SUMMARY OF THE INVENTION

In various embodiments, the present invention features apparatus and methods for emptying, rinsing, and filling, in situ, a drug reservoir of a drug-delivery device implanted within a patient's body via one or more self-sealing, needle-accessible fill ports. The drug-delivery device may be, for example, an implantable drug-delivery pump. The apparatus generally contain features, and the methods typically involve steps, that allow the emptying, rinsing, and filling to occur in a manner that minimizes the risk of damage to the pump, and thereby maximizes its effective lifetime. For example, in one embodiment, a dedicated refill instrument allows multiple fluids to be controlled and directed through a single fill port of the drug-delivery pump and with only a single needle insertion. In addition, the refilling process may be automated so as to protect pump components from potential damage and ensure reliable and repeatable refilling.

In various embodiments, the fill port(s) of the implantable pump itself contain various features that, either alone or in combination, promote the reliable and repeatable refilling of the implantable drug-delivery pump. For example, as described herein, the fill port(s) may contain features that prevent the backflow of drug from the drug reservoir through the fill port.

In general, in one aspect, embodiments of the invention feature an implantable drug-delivery pump. The pump includes a drug reservoir and, in fluid communication therewith, a fill port that includes an elastomeric plug. The plug extends at least partially through an aperture in a wall of the fill port. The pump also includes means for enhancing retainment of the plug within the aperture (e.g., grooves or threads, or other features that promote mechanical interlocking, in the aperture). In various embodiments, the pump also includes a parylene coating in or over the aperture.

In general, in another aspect, embodiments of the invention feature another implantable drug-delivery pump. Again, this pump includes a drug reservoir and, in fluid communication therewith, a fill port that includes an elastomeric plug extending at least partially through an aperture in a wall of the fill port. Moreover, the pump also includes a check valve, closeable over the aperture, for preventing backflow from the reservoir through the fill port. The check valve may include a pair of parylene flaps or a single parylene flap closable over the aperture.

In either pump, the wall through which the aperture of the fill port is formed may be the same as a wall that surrounds, at least partially, the drug reservoir. Alternatively, tubing may be employed to connect the aperture of the fill port to the drug reservoir. In various embodiments, the plug is made of silicone. The fill port may include a needle guide for guiding a needle therethrough. Furthermore, the fill port may have a geometry that is compatible only with needles having a complementary geometry.

In general, in yet another aspect, embodiments of the invention feature an implantable drug-delivery pump that includes a drug reservoir, a cannula for conducting liquid from the reservoir to a target site, an electrolyte chamber, an expandable diaphragm that separates the chamber and the reservoir and that provides a fluid barrier therebetween, and a plurality of fill ports for providing external access to at least one of the reservoir or the chamber. For example, a first fill port may provide external access to the reservoir and a second fill port may provide external access to the chamber. Alternatively or in addition, at least two fill ports may each provide external access to the reservoir and/or at least two fill ports may each provide external access to the chamber.

In general, in still another aspect, embodiments of the invention feature a tool for refilling an implantable drug-delivery pump, such as a pump as described above. The tool includes first and second independent fluid channels, a fluid reservoir in fluid communication with the first fluid channel, first and second pumps each fluidly coupled to one of the fluid channels, and means for engaging a fill port of the implantable drug-delivery pump. The first pump may be configured to apply positive pressure to the first fluid channel so as to drive fluid from the fluid reservoir therethrough, and the second pump may be configured to apply negative pressure to the second fluid channel. For its part, the engaging means may be a needle that is configured for insertion into the fill port. The needle may have a lumen in fluid communication with the first and second fluid channels.

In various embodiments, the tool further includes a third independent fluid channel, a second fluid reservoir in fluid communication therewith, and a third pump fluidly coupled to the third fluid channel. In such a case, the third pump may be configured to apply positive pressure to the third fluid channel so as to drive fluid from the second fluid reservoir therethrough.

The tool may also include governing circuitry that prevents fluid pressure at an outlet of the needle lumen from exceeding a predefined level. First and second valves, responsive to the governing circuitry, may also be included to control fluid flow through the first and second fluid channels, respectively. Moreover, the tool may include a bubble detector and/or a degasser in at least one of the first, second, or third fluid channels. The bubble detector may be, for example, an ultrasonic bubble detector, an optical bubble detector, a thermal bubble detector, or an electrical bubble detector.

In another embodiment, the needle features first and second lumens therethrough. The first and second lumens may be fluidly isolated from each other. The first lumen may communicate with the first fluid channel, and the second lumen may communicate with the second fluid channel.

In general, in still another aspect, embodiments of the invention feature a method of filling an implantable drug-delivery pump having a drug chamber. In accordance with the method, a tool is first provided. The tool includes first and second independent fluid channels, and a fluid reservoir in fluid communication with the first fluid channel. The tool may be coupled to a fill port of the implantable drug-delivery pump, and then be used to purge the drug chamber and subsequently pump fluid from the fluid reservoir into the drug chamber via the first fluid channel without exceeding a maximum pressure in the drug chamber.

In various embodiments, the tool is coupled to the fill port by means of a needle that has a lumen in fluid communication with the first and second fluid channels. The purging step may include pumping fluid from the fluid reservoir into the drug chamber via the needle and the first fluid channel and thereafter suctioning the fluid from the drug chamber via the needle and the second fluid channel. In another embodiment, the tool further includes a third independent fluid channel and a second fluid reservoir in fluid communication therewith, and the purging step involves pumping fluid from the second fluid reservoir into the drug chamber via the needle and the third fluid channel, and thereafter suctioning the fluid from the drug chamber via the needle and the second fluid channel.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations, even if not made explicit herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 5A-5E schematically illustrate, in cross-section, a process for manufacturing yet another variant of a fill port in accordance with one embodiment of the invention;

FIGS. 6A-6D schematically illustrate, in cross-section, the internal structure of various fill ports having needle stops in accordance with embodiments of the invention;

FIG. 7 schematically illustrates, in cross-section, the internal structure of a fill port having a needle guide in accordance with one embodiment of the invention;

DESCRIPTION

In general, embodiments of the present invention pertain to drug-delivery pumps implantable within a patient's body, such as, for example, within the patient's eye or brain, and to apparatus and methods for refilling those pumps. In certain embodiments, the implantable drug-delivery pumps combine small size and a refillable drug reservoir. The small size minimizes discomfort from the drug-delivery pump to the patient, while the refillable reservoir allows the pump to be refilled in situ, rather than having to be replaced. As such, a fluid, such as a solution of a drug, can be supplied to the patient over extended periods of time.

Figure 1A:
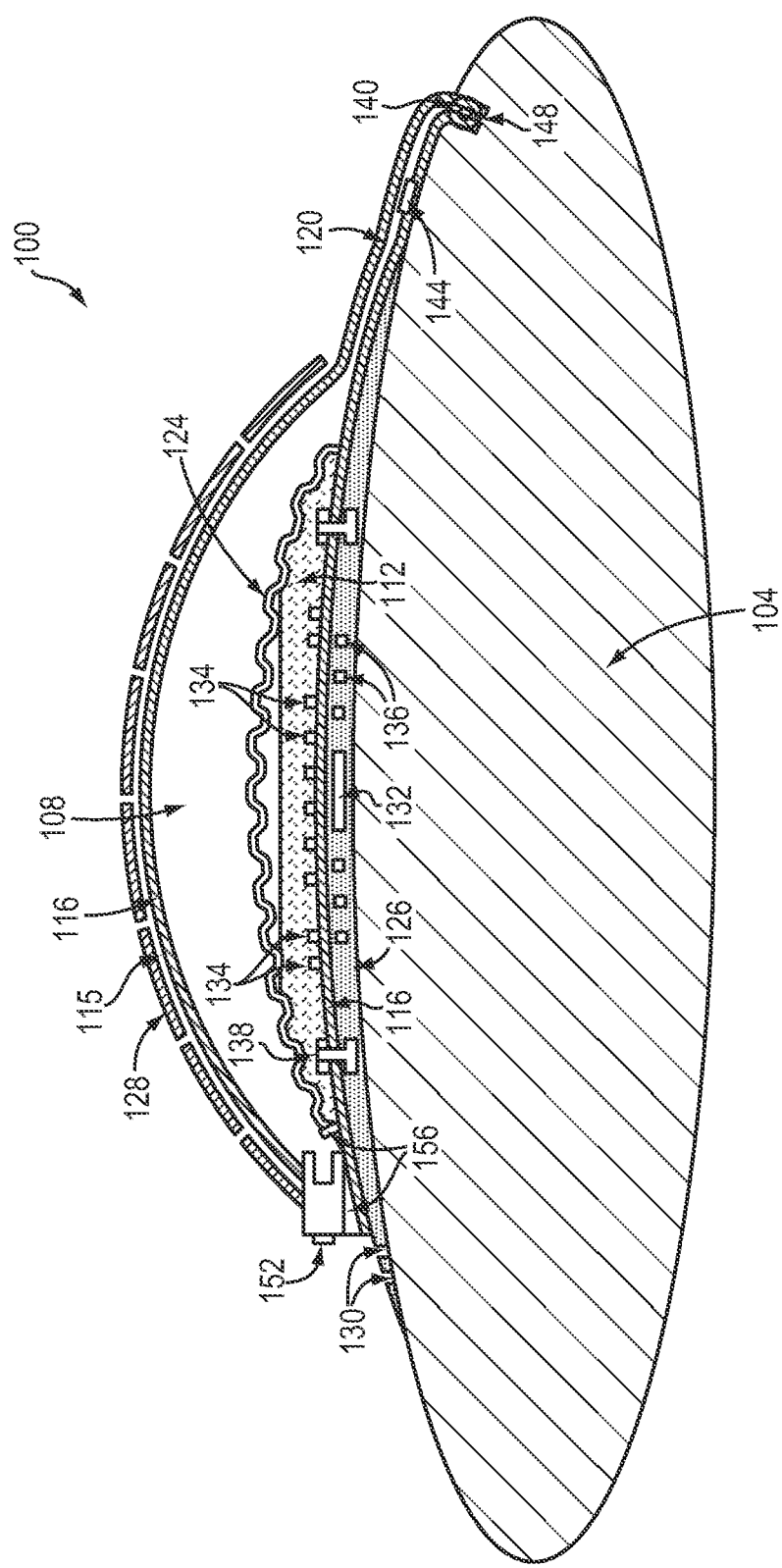
FIG. 1A schematically illustrates, in cross-section, an implantable drug-delivery device in accordance with one embodiment of the invention.
Figure 1B:
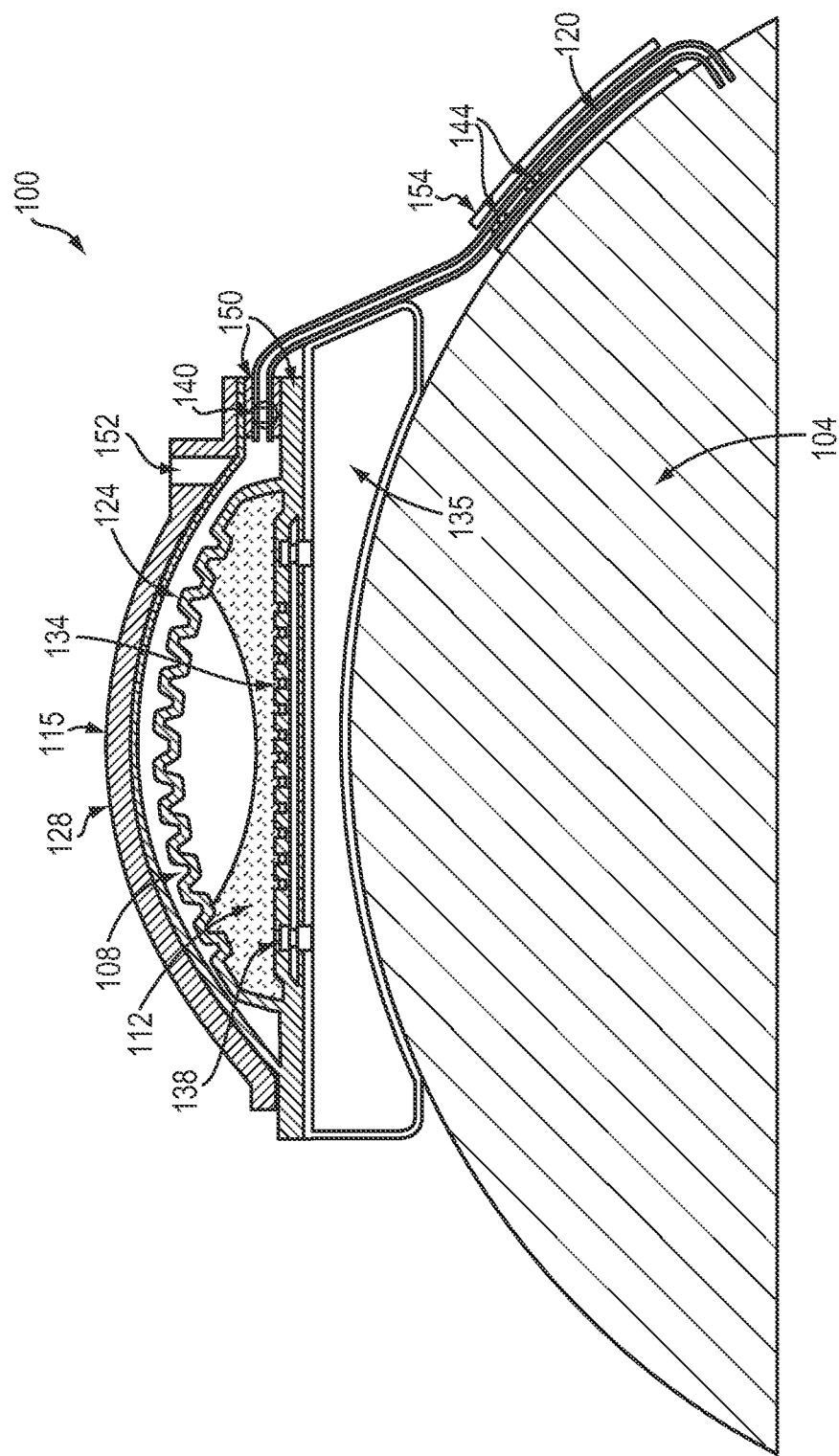
FIG. 1B schematically illustrates, in cross-section, an implantable drug-delivery device in accordance with another embodiment of the invention.

Embodiments of the invention may be employed in connection with various types of implantable drug-delivery pumps. FIGS. 1A and 1B schematically illustrate two variations of one such implantable drug-delivery pump 100 (namely, an exemplary electrolytic pump 100) implanted within a patient's eye 104. The pump 100 may instead, however, be implanted in other portions of a patient's body. For example, it may be implanted in the sub-arachnoid space of the brain to provide chemotherapy or to provide another type of treatment for the brain (e.g., by dosing the brain's parenchyma directly), or near a tumor in any portion of the patient's body to provide chemotherapy, or in a pancreas that does not respond well to glucose to provide agents (e.g., proteins, viral vectors, etc.) that will trigger insulin release, or in the knee to provide drugs that will treat osteoarthritis or other cartilage diseases, or near the spine to provide pain medications or anti-inflammatories, or elsewhere. As illustrated in FIGS. 1A and 1B, embodiments of the pump 100 may include two main components: a pair of chambers 108, 112 surrounded, at least in part, by a wall 115, and a cannula 120. As illustrated in FIG. 1A, the wall 115 that surrounds the chambers 108, 112 may include or consist of a stand-alone parylene film 116 and, thereover, a separate protection shell 128 made of a relatively rigid biocompatible material (e.g., medical-grade polypropylene). Alternatively, as illustrated in FIG. 1B, the wall 115 may correspond only to the protective shell 128, which may be coated with parylene. The top chamber 108 defines a drug reservoir that, when being used to treat a patient, may contain the drug to be administered in liquid form. For its part, the bottom chamber 112 may contain a liquid that, when subjected to electrolysis, evolves a gaseous product. For example, that liquid may be water, which may be electrolytically separated by an applied voltage into hydrogen gas and oxygen gas. Alternatively, as other examples, the electrolyte liquid may be a saline solution (i.e., NaCl and $H_2O$) or a solution that contains either magnesium sulfate or sodium sulfate. In one embodiment, the two chambers 108, 112 are separated by a corrugated diaphragm 124. In other words, the diaphragm 124 provides a fluid barrier between the two chambers 108, 112. Like the stand-alone film 116, the diaphragm 124 may be constructed from, for example, parylene.

As illustrated in FIG. 1A, the stand-alone film 116 may act as an outer barrier for the drug reservoir 108 and the protective shell 128 may provide a hard surface against which the film 116 exerts pressure. In such a case, the shell 128 may be perforated to allow for eye, brain, or other bodily fluid movement. Alternatively, as illustrated in FIG. 1B, the protective shell 128 may itself act as the outer barrier for the drug reservoir 108 and be unperforated. In both embodiments depicted in FIGS. 1A and 1B, the protective shell 128 may prevent outside pressure from being exerted on the drug reservoir 108. As illustrated in FIG. 1A, a bottom portion 126 (i.e., a floor 126) of the protective shell 128 may include suture holes 130. Similarly, although not shown in either FIG. 1A or FIG. 1B, the cannula 120 may also include suture holes along its sides. The suture holes 130 may be employed in suturing (i.e., anchoring) the pump 100 in place in the patient's body.

As also illustrated in FIG. 1A, to provide power to the pump 100 and to enable data transmission therewith, a battery and control circuitry 132 may be embedded (e.g., hermetically sealed) under the chambers 108, 112 (i.e., between a bottom portion of the stand-alone parylene film 116 of the drug reservoir 108 and the floor 126 of the protective shell 128), and an induction coil 136 may be integrated in the protective shell 128 (e.g., by injection molding). FIG. 1B more clearly illustrates a hermetic case 135 for housing the battery and conventional control circuitry 132, but, for simplicity, does not depict the components housed therein. The hermetic case 135 may be made from biocompatible metals (e.g., titanium) or metal alloys. The bottom of the hermetic case 135 may be flat, or it may be concave to help the implantable pump 100 fit on the patient's eye 104.

In one embodiment, the induction coil 136 permits wireless (e.g., radio-frequency) communication with an external device (e.g., a handset). The handset may be used to send wireless signals to the control circuitry 132 in order to program, reprogram, operate, calibrate, or otherwise configure the pump 100. In one embodiment, the control circuitry 132 communicates electrically with electrolysis electrodes 134 in the electrolyte chamber 112 by means of metal interconnects (vias) 138 spanning a bottom portion of the electrolyte reservoir 112. The electrolysis electrodes 134 may be made from, for example, platinum, gold, and/or other metal(s). As further described below, the control circuitry 132 controls the pumping action of the pump 100, including the below-described closed-loop control process.

In one embodiment, as illustrated in FIG. 1A, the cannula 120 connects the drug chamber 108 to a check valve 140 inserted at the site of administration. Alternatively, or in addition, as illustrated in FIG. 1B, the check valve 140 may be integral with and located at a proximal end of the cannula 120 (i.e., at the end closest to the drug reservoir 108). One or more flow sensors 144 for monitoring the flow of the drug—and thereby enabling the measurement of drug volume—through the cannula 120 may be associated with one or more of a proximal, middle, or distal portion of the cannula 120. Optionally, as illustrated in FIG. 1A, a pressure sensor 148 may also be integrated at a distal end of the cannula 120 (i.e., at the end furthest from the drug reservoir 108) in order to measure pressure at the site of administration (e.g., the intravitreal chamber, shoulder capsule, knee capsule, cerebral ventricals, spinal canal, etc.). In one embodiment, the pressure sensor 148 provides feedback to the control circuitry 132 so that the flow of drug may be metered by a closed-loop control process. For example, increased pressure in the drug target region may cause a decrease in the flow of drug from the pump 100.

As illustrated in FIG. 1A, the cannula 120 may be an extension of the stand-alone parylene film 116. Alternatively, as illustrated in FIG. 1B, the cannula 120 may be a separate component coupled to the protective shell 128. For example, a proximal end of the cannula 120 may be inserted through a fluid connection port formed in the protective shell 128 and bonded thereto by way of, e.g., a biocompatible epoxy glue 150. A silicone sheath 154 may be placed around a portion of the cannula 120 (see FIG. 1B), but this is optional (see FIG. 1A).

In one embodiment, as illustrated in FIG. 1A, a fill port 152 is assembled with the drug reservoir 108 and sealed by a sealant (e.g., a biocompatible epoxy) 156 to the stand-alone film 116 and protective shell 128. In yet another embodiment, as illustrated in FIG. 1B, a hole may be formed through the protective shell 128 and the fill port 152 featured therein. In still another embodiment, the fill port 152 may be formed elsewhere on the pump 100 and connected to the drug reservoir 108 through tubing. For example, the fill port 152 may be molded from biocompatible materials, coupled to a matching notch on the hermetic case 135, and connected to the drug reservoir 108 through the tubing. In one embodiment, the tubing is inserted through a fluid connection port formed in a wall surrounding the drug reservoir 108 and bonded thereto by way of a biocompatible epoxy glue. In either case, as described further below, the fill port 152 is in fluid communication with the drug reservoir 108 and permits an operator of the pump 100 (e.g., a physician) to refill the drug reservoir 108 in situ (e.g., while the pump 100 is implanted within the patient's eye 104). In general, the drug reservoir 108 can be refilled by inserting a refill needle into and through the fill port 152.

In various embodiments, the main parts of the pump 100 (i.e., the pair of chambers 108, 112 and the cannula 120) are amenable to monolithic microfabrication and integration using multiple parylene layer processes. The fill port 152, the protective shell 128, and other components may be assembled with the pump 100 after the microfabrication steps.

In operation, when current is supplied to the electrolysis electrodes 134, the electrolyte evolves gas, expanding the corrugated diaphragm 124 (i.e., moving the diaphragm upwards in FIGS. 1A and 1B) and forcing liquid (e.g., drug) to be conducted out of the drug reservoir 108, through the cannula 120, and out the distal end thereof to the targeted site of administration. The corrugations or other folds in the expandable diaphragm 124 permit a large degree of expansion, without sacrificing volume within the drug reservoir 108 when the diaphragm 124 is relaxed. When the current is stopped, the electrolyte gas condenses back into its liquid state, and the diaphragm 124 recovers its space-efficient corrugations.

Figure 2:
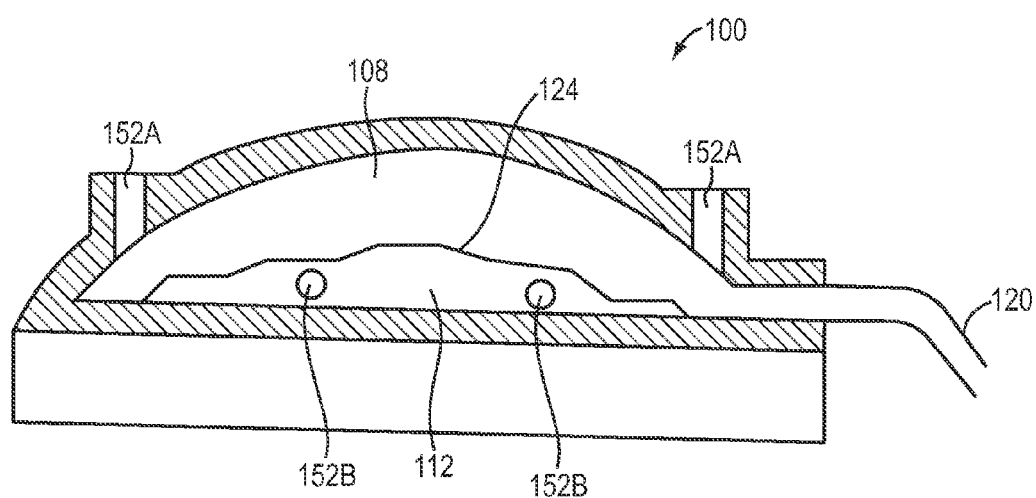
FIG. 2 schematically illustrates an implantable drug-delivery device, having multiple fill ports, in accordance with yet another embodiment of the invention.

In some embodiments, with reference to FIG. 2, the implantable pump 100 includes a plurality of fill ports 152. For example, the pump 100 may include a first, single fill port 152A that provides external access to the drug reservoir 108 and a second, single fill port 152B that provides external access to the electrolyte chamber 112. In this way, either chamber 108, 112 may be refilled when depleted (e.g., as sensed by the control circuitry 132). Alternatively, the pump 100 may include (i) two or more fill ports 152A providing external access to the drug reservoir 108 and no or a single fill port 152B providing external access to the electrolyte chamber 112, or (ii) two or more fill ports 152B providing external access to the electrolyte chamber 112 and a single fill port 152A (or no fill port) providing external access to the drug reservoir 108, or (iii) two or more fill ports 152A providing external access to the drug reservoir 108 and two or more fill ports 152B providing external access to the electrolyte chamber 112. In one embodiment, multiple fill ports 152 for a single chamber 108, 112 facilitate the emptying, rinsing, and/or filling of the chamber 108, 112 (e.g., to extract trapped air, etc.), with one fill port receiving new fluid as existing fluid exits another fill port. The multiple fill ports 152A, 152B may be integrated with the pump 100 as described above (e.g., formed through the protective shell 128; coupled to the pump 100 in another location and connected to the drug reservoir 108 or electrolyte chamber 112, as the case may be, through tubing; etc.).

Figure 3A:
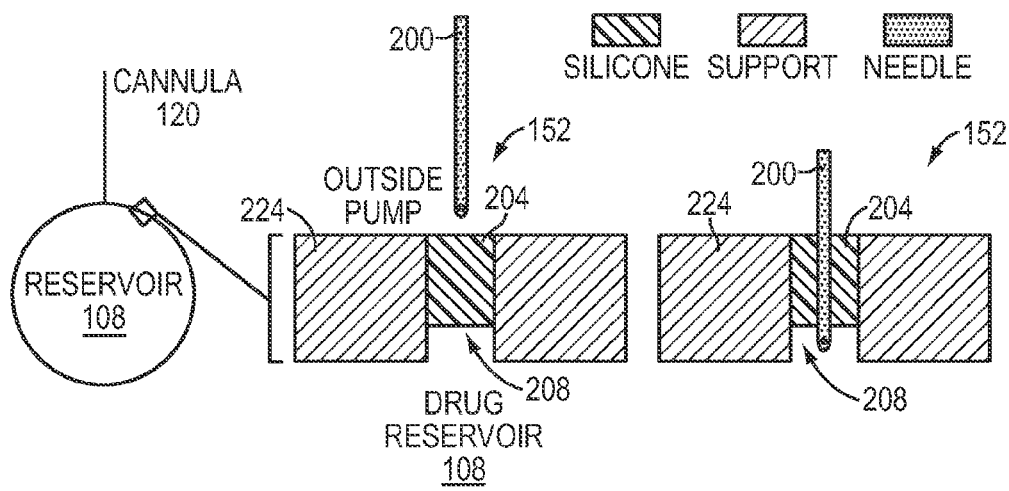
FIG. 3A schematically illustrates, in cross-section, the internal structure of a fill port in accordance with one embodiment of the invention, as it is pierced by a refill needle.
Figure 3B:
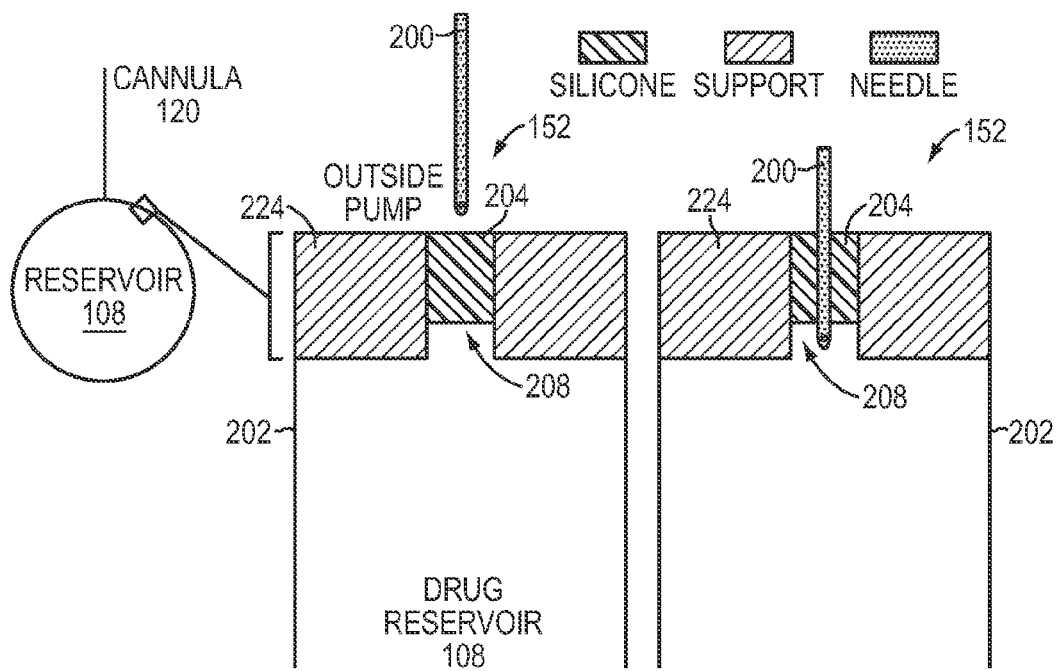
FIG. 3B schematically illustrates, in cross-section, the internal structure of a fill port that is connected by tubing to a drug reservoir in accordance with one embodiment of the invention, as the fill port is pierced by a refill needle.

FIG. 3A schematically illustrates the internal structure of a fill port 152, in accordance with one embodiment of the invention, as it is pierced by a refill needle 200. The fill port 152 is illustrated in FIG. 3A as being in fluid communication with the drug reservoir 108. However, as described above, the fill port 152 may instead be in fluid communication with the electrolyte chamber 112. Moreover, rather than being in direct contact with the drug reservoir 108 or electrolyte chamber 112, the fill port 152 may instead be connected thereto through intermediary tubing 202, as illustrated in FIG. 3B. Accordingly, it will be understood by one of ordinary skill in the art that the following description of the various embodiments of the fill port 152 and of the various embodiments of refilling the drug reservoir 108 using the fill port 152 also apply equally to a fill port 152 that is in fluid communication with the electrolyte chamber 112 (either directly or through use of the intermediary tubing 202) and to methods of refilling the electrolyte chamber 112 using the fill port 152.

As illustrated in FIGS. 3A and 3B, one embodiment of the fill port 152 includes an elastomeric plug 204 that is molded inside a hollow structure 208 defined by a wall 224 of the fill port 152. Where the fill port 152 is in fluid communication with the drug reservoir 108 without the use of the tubing 202 (FIG. 3A), the hollow structure 208 may in fact be an aperture that spans the thickness of the protective shell 128 and/or the stand-alone film 116. As shown in FIGS. 3A and 3B, the elastomeric plug 204 may extend at least partially through the aperture 208. In one embodiment, the diameter and thickness of the elastomeric plug 204 is generally less than 3 mm.

The elastomeric plug 204 may be, for example, a silicone plug 204 (as indicated in FIGS. 3A and 3B). More generally, however, the plug 204 may be made from any material (e.g., soft plastic) that that can be punctured with the needle 200 and that is capable of re-sealing itself upon removal of the needle 200. Moreover, the self-sealing material of the plug 204 may be able to withstand multiple punctures by the needle 200, and may be biocompatible. In addition to silicone, materials from which the plug 204 may be manufactured include, but are not limited to, polydimethylsiloxane ("PDMS"), parylene C, parylene HT, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, and porous rubbers.

In one embodiment, to form the silicone plug 204, uncured silicone rubber is directly injected inside the hollow structure 208 and cured in place. The self-sealing properties of the silicone rubber allow the needle 200 to be inserted into and withdrawn from the fill port 152 without causing any permanent leaks.

Figure 4A:
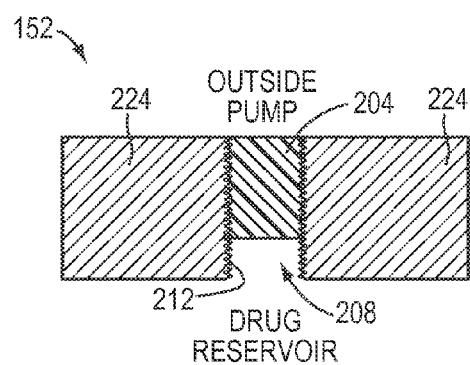
FIGS. 4A-4D schematically illustrate, in cross-section, the internal structure of various fill ports in accordance with further embodiments of the invention.

The fill port 152 illustrated in FIGS. 3A and 3B includes a smooth-bore aperture 208. In some embodiments, however, the fill port 152 further includes means for enhancing retainment of the plug 204 within the aperture 208. For example, as shown in the fill port 152 illustrated in FIG. 4A, threads, grooves or other features 212 facilitating mechanical interlocking may be machined on or molded into the walls 224 that define the aperture 208 to keep the plug 204 secured in place. These features 212 increase the sealing surface area and also mechanically anchor the plug 204 in place.

Figure 4C:
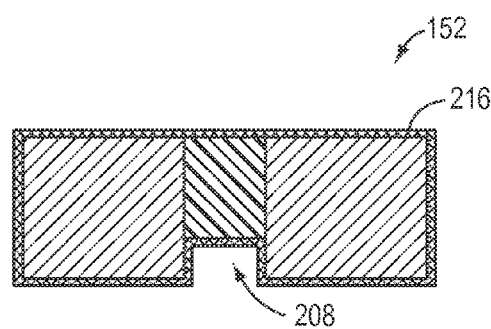
Figure 4B:
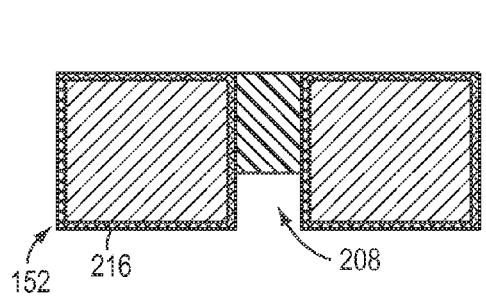
Figure 4D:
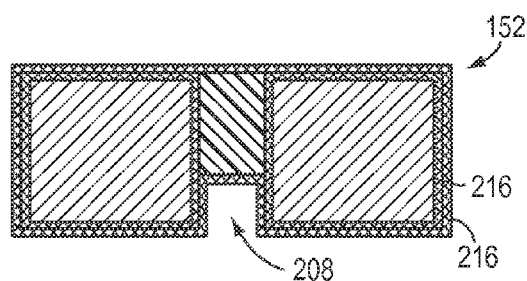

In addition, where the plug 204 is made of a polymer (e.g., silicone) that is capable of leaching or absorbing drugs that come into contact with it, the fill port 152 may be coated with a biocompatible polymer (e.g., parylene) so that less drug is exposed to the polymer. The coating 216 also aids to minimize the possibility of leaking at the plug/support interface. The parylene coating 216 may be applied before, after, or both before and after the formation of the plug 204 so that the parylene coating 216 is applied inside, over, or both inside and over the aperture 208, respectively. For example, the fill port 152 depicted in FIG. 4B features a silicone plug 204 molded inside a smooth-bore aperture 208 that has a single parylene coating 216 inside the aperture 208, the fill port 152 depicted in FIG. 4C features a silicone plug 204 molded inside a smooth-bore aperture 208 that has a single parylene coating 216 over (and only partially inside) the aperture 208, and the fill port 152 depicted in FIG. 4D features a silicone plug 204 molded inside a smooth-bore aperture 208 that has a dual parylene coating 216 (both inside and over the aperture 208).

In yet another embodiment, the parylene coating 216 may be applied inside in aperture 208 and over a bottom portion thereof, but not over a top portion of the aperture 208. Such a structure for the fill port 152 is illustrated in FIG. 5E, while FIGS. 5A-5D schematically illustrate the steps in an exemplary process for manufacturing the structure depicted in FIG. 5E. In greater detail, with reference first to FIG. 5A, a parylene coating 216 is first applied to the aperture 208 of the fill port 152 and, thereafter, the plug 204 is formed therein. Then, as illustrated in FIG. 5B, the top surface of the fill port 152 is masked by applying a further segment 226 of silicone thereto. Subsequently, a second parylene coating 216 may be applied (FIG. 5C) and the further segment 226 of silicone stripped away from the fill port 152 (FIG. 5D), leaving the structure depicted in FIG. 5E. Advantageously, the use of the silicone segment 226 prevents the second parylene coating 216 from covering the top surface of the aperture 208. One reason for which such a structure is desirable is that it prevents the second parylene coating 216 from being dragged into the plug 204 during needle 200 insertion. Dragging the parylene coating 216 into the plug 204 may, for example, damage the fill port 152 and lead to the leakage of fluid therefrom.

With reference now to FIGS. 6A-6D, in some cases it is desirable to have a needle stop 220 positioned within the fill port 152. As illustrated, the stop 220 may extend at least partially into the aperture 208. The stop 220 may be integrally formed with the wall 224 of the fill port 152 or may be a separately manufactured piece that is secured to the wall 224 by, for example, by gluing the stop 220 to the wall 224 with an epoxy or other suitable adhesive. In this way, the progress of the refill needle 200 into the fill port 152 halts when a tip of the needle 200 contacts the stop 220. This prevents the needle 200 from being inserted too far into the pump 100, which could cause damage thereto.

The stop 220 may take the form of a mechanical plate (e.g., as illustrated in FIGS. 6A and 6D), a filter (e.g., as illustrated in FIG. 6C), a bend (e.g., as illustrated in FIG. 6B), or any number of other structures whose shape is suitable for carrying out the functions of the stop 220 described herein. Moreover, as illustrated in FIGS. 6A and 6D, the top surface of the stop 220 may be flat. Alternatively, the top surface of the stop 152 may be cup-shaped or concave. In this way, the stop 220 may also aid in preventing the refill needle 200 from contacting, and possibly penetrating, one of the sidewalls 224 defining the aperture 208.

The fill port 152 and the needle stop 220 thereof can also be designed so that only certain needles 200 can be used to access the drug reservoir 108. In other words, the fill port 152 may be designed to have a geometry that is compatible only with needles 200 having a complementary geometry. For example, as illustrated in FIG. 6D, an exit hole of the needle 200 only matches with an access channel 228 when the needle 200 is fully inserted to the needle stop 220. And, as illustrated in FIGS. 6A-6C, the exit hole of the needle 200 only matches with an area of the aperture 208 not occupied by the plug 204 when the needle 200 is fully inserted to the needle stop 220.

In general, the stop 220 of the fill port 152 may be constructed of any relatively rigid and mechanically robust material, or combinations of materials, that has/have the requisite mechanical strength for performing the functions of the stop 220 described herein. For example, the stop 220 may be constructed of a metal, a hard (e.g., fully cross-linked or reinforced) plastic, a composite material, or a combination thereof. More specific examples of materials for the stop 220 include a thick layer of PDMS, polyimide, polypropylene, polyaryletheretherketone ("PEEK"), polycarbonate, acetyl film (e.g., acetyl copolymer), polyoxymethylene plastic (e.g., DELRIN), gold, stainless steel, nickel, and/or chrome. The stop 220 may (but need not necessarily) be biocompatible.

Because the fill port 152 may be of relatively small size, it may be desirable, in some embodiments, for the fill port 152 to also include a needle guide to ensure that the needle 200 is inserted substantially straight into the fill port 152. While there is some room for error, too large an entry angle may cause the needle 200 to strike the support structure for the fill port 152 (i.e., the wall 224), and to miss penetrating the elastomeric plug 204. As illustrated in FIG. 7, the needle guide 232 may be conically shaped, or may have another shape. In addition, the needle guide 232 may be integrally formed with the fill port 152, or it may be removable and be placed on top of the fill port 152, and mechanically or magnetically locked thereto, just prior to the refilling procedure.

In another embodiment, the implantable drug-delivery pump 100 also includes a check valve, for example within the drug reservoir 108 or within the intermediary tubing 202 and closeable over the aperture 208, for preventing backflow from the reservoir 108 through the fill port 152. The check valve may also rectify the flow of drug from the needle 200 into the drug reservoir 108 and reduce the possibility of leakage. In one embodiment, the check valve opens as liquid is pushed into the drug reservoir 108, and thereafter closes.

Figure 8:
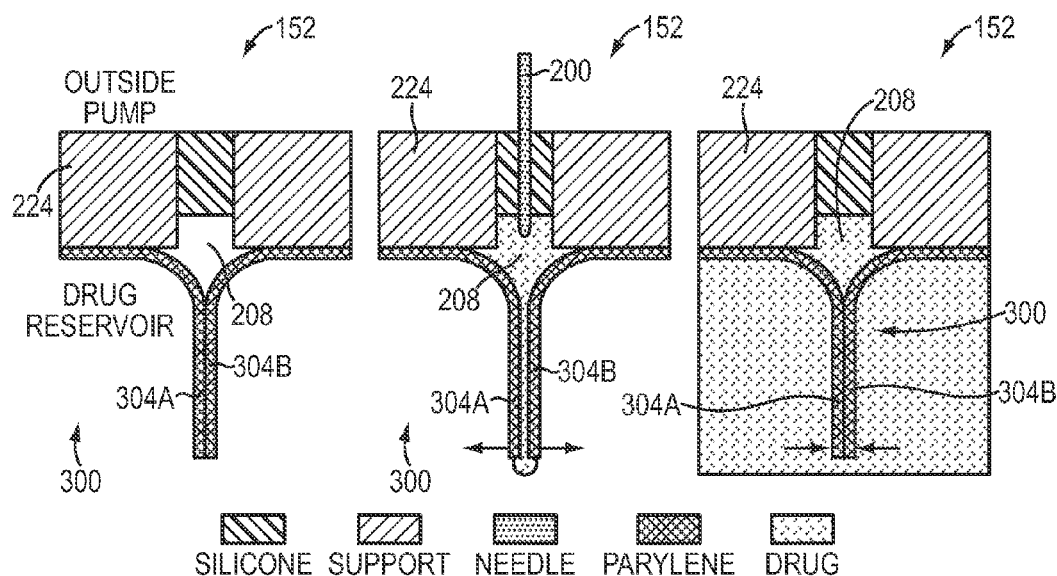
FIG. 8 schematically illustrates, in cross-section, the internal structure of a fill port having a pair of flaps as a check valve in accordance with one embodiment of the invention, as drug is delivered thereto.
Figure 9:
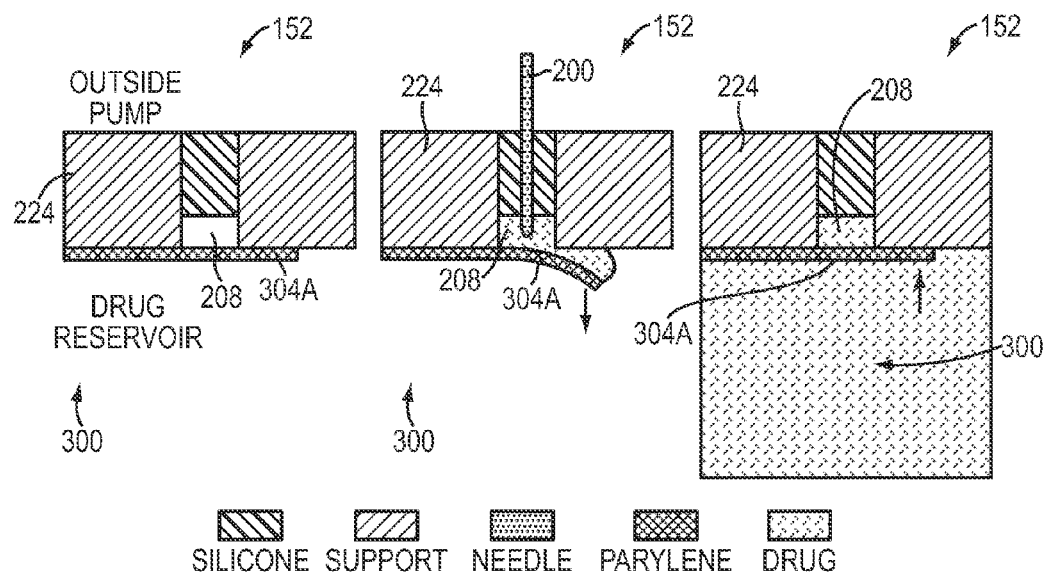
FIG. 9 schematically illustrates, in cross-section, the internal structure of a fill port having a single flap as a check valve in accordance with one embodiment of the invention, as drug is delivered thereto.

Two exemplary check valve designs are depicted in FIGS. 8 and 9. The illustrated check valves 300 include one (FIG. 9) or two (FIG. 8) flaps 304A, 304B of a biocompatible polymer, such as parylene. The flap(s) 304A, 304B may be bonded to the bottom surface of the fill port's wall 224 using, for example, an adhesive, thermal bonding, ultrasonic bonding, laser welding, etc. As illustrated in FIG. 8, the flaps 304A, 304B are forced apart (or a single flap 304 is displaced from the aperture 208, as illustrated in FIG. 9), as liquid is injected into the drug chamber 108 from the refill needle 200. After withdrawal of the needle 200, the pressure exerted on the flap(s) 304A, 304B by the injected liquid will keep the check valve 300 closed over the aperture 208, thus preventing any backflow of liquid through the fill port 152. While in FIGS. 8 and 9 the fill ports 152 are shown to have an uncoated smooth-bore aperture 208 design, it will be understood by one of ordinary skill in the art that the fill ports 152 may in fact have any of the above-described configurations (e.g., have threaded or grooved sidewalls, be parylene-coated, etc.).

Embodiments of the invention also facilitate filling or refilling the drug reservoir 108 of the implantable drug-delivery device 100 described above. Through a fill port 152 of the pump 100, any remaining liquid may be removed, the drug reservoir 108 washed, and the new drug injected. Accordingly, embodiments of the invention may feature an external tool that interfaces with the implantable drug-delivery pump 100 to facilitate automated refilling of the drug reservoir 108. Filling or refilling of the drug reservoir 108 may occur while the pump 100 is implanted within the patient's body (e.g., within the patient's eye 104) and may involve procedures for emptying, washing, and filling or refilling the drug chamber 108. As described below, these processes may be performed using a tool that features either a single-lumen or a dual-lumen needle.

Figure 10:
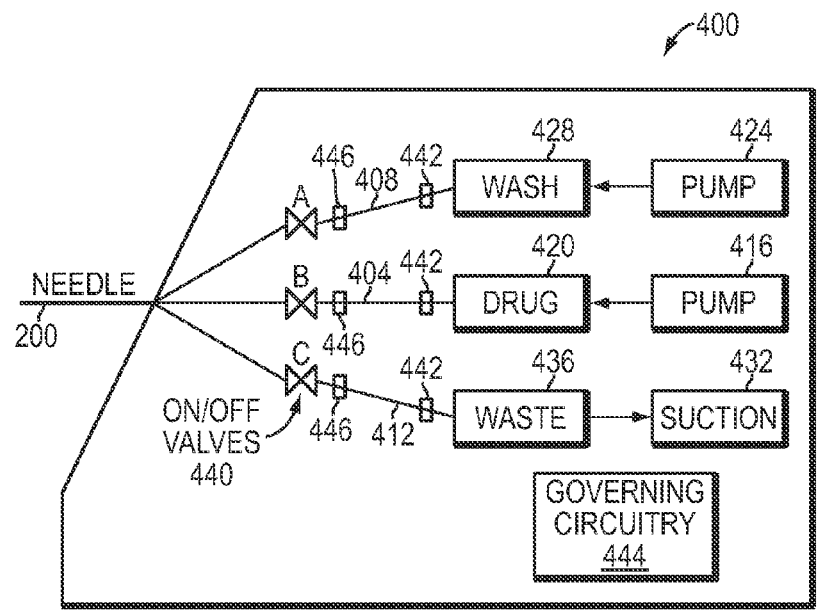
FIG. 10 schematically illustrates a tool for refilling an implantable drug-delivery device in accordance with one embodiment of the invention.

A tool for interfacing to and refilling a drug reservoir 108 as described herein may have two, three, or more independent fluid channels. For example, the tool 400 depicted in FIG. 10 includes three independent fluid channels 404, 408, 412. The first channel 404 is in fluid communication with a first pump 416 that handles the drug 420. The second channel 408 is in fluid communication with a second pump 424 that handles a rinse solution 428. The third channel 412 uses vacuum suction 432 to remove or aspirate fluid waste 436 from the drug reservoir 108. Fluid flow through all three channels 404, 408, 412 can be effected using standard mechanical pumping technologies (e.g., gear, diaphragm, peristaltic, syringe, etc.). The flows can also be pneumatically controlled through the application of pressure or vacuum to the individual channels 404, 408, 412. As illustrated in FIG. 10, these three fluid channels 404, 408, 412 may be interfaced to a flow-switching or valving system 440 and ultimately terminate in the needle 200, which is used to pierce the elastomeric plug 204 of the fill port 152 and access the drug reservoir 108.

In addition, in one embodiment, one, more, or all of the channels 404, 408, 412 include a bubble detector 442 and/or an in-line degasser 446. Each of the detector 442 and the degasser 446 may be located upstream of the valving system 440, as depicted in FIG. 10. Alternatively, one or both of the detector 442 and degasser 446 may in fact be located downstream of the valving system 440. As such, the order in which the various components of the tool 400 are shown to be placed in FIG. 10 is non-limiting.

In one embodiment, the bubble detector 442 serves to detect gas in its respective channel 404, 408, 412. The presence of gas inside the drug reservoir 108 could cause the pump 100 to malfunction. Advantageously, upon detection by a bubble detector 442 of a gas bubble in one of the channels, 404, 408, 412, the detector 442 may signal (e.g., to governing circuitry 444, described further below) the presence of such gas. The filling/refilling of the drug reservoir 108 may then be stopped, the needle 200 removed from the fill port 152, and the tool 400 flushed to remove any and all gas.

A bubble detector 442 may be implemented through a variety of means, including, but not limited to, ultrasonic, optical, thermal, or electrical. For example, an ultrasonic bubble detector 442 may be placed in proximity, but not in contact, with fluid flowing through a channel 404, 408, 412, transmit ultrasonic energy through the flowing fluid, and sense the amount of energy transmitted therethrough. The amount of energy transmitted through the fluid will change when there is gas present in the fluid. Suitable ultrasonic bubble detectors 442 may be provided by, for example, Introtek International of Edgewood, N.Y.; Zevek, Inc. of Salt Lake City, Utah; and Cosense, Inc. of Hauppauge, N.Y.

An optical detector 442 may also be placed in proximity, but not in contact, with fluid flowing through a channel 404, 408, 412, shine light (e.g., infra-red light) through the flowing fluid, and sense the amount of light transmitted therethrough. Again, the amount of light transmitted through the fluid will change when there is gas present in the fluid.

For its part, a thermal detector 442 may be placed in contact with (or in proximity to, but not in contact with) the fluid. The thermal detector 442 may then heat (e.g., through use of a heater) fluid flowing passed the detector 442 and sense the temperature of the fluid at, for example, a downstream location. The different thermal properties of a flowing fluid, as opposed to a flowing fluid comprising gas, will result in different temperatures for each being sensed downstream. Accordingly, the temperature sensed downstream may indicate the presence or absence of gas in the fluid. Suitable thermal bubble detectors 442 may be provided by, for example, Sensirion AG of Switzerland.

Finally, an electrical detector 442 may measure some electrical property of the fluid flowing through the channel 404, 408, 412. For example, the electrical detector 442 may measure the dielectric constant, resistivity, etc. of the flowing fluid. The reading may provide an indication of the presence, or absence, of gas in the fluid.

For its part, a degasser 446 may automatically remove any and all gas from its respective channel 404, 408, 412. For example, the degasser 446 may be implemented as a semipermeable membrane (e.g., permeable to gas, but not to fluid) in a wall of its respective channel 404, 408, 412. Gas present in that channel would then be expelled from the channel through the membrane. In addition, a vacuum may be applied to the membrane wall outside the channel 404, 408, 412 to speed up the gas removal process.

While FIG. 10 depicts a tool 400 having three independently controlled fluid channels 404, 408, 412, it is possible in some cases, as mentioned, to use fewer. For example, instead of using a dedicated wash solution 428 to rinse the drug reservoir 108, the drug solution 420 can itself be used for that purpose. In these embodiments, two independent fluid channels 404, 412—one (404) for infusing the drug 420 and a second (412) for aspirating liquid 436 out of the reservoir 108—will suffice.

The tool 400 may also include governing circuitry 444 to control and actuate the first and second pumps 416, 424, the vacuum suction 432, the flow-switching or valving system 440, the bubble detectors 442, and/or the vacuums interfacing with the degassers 446. The control logic underlying the governing circuitry 444 may be implemented as any software program, hardware device, or combination thereof that is capable of achieving the functionality described herein. For example, the governing circuitry 440 may be an application-specific integrated circuit (ASIC) or a field programmable gate array (FPGA). Alternatively, the governing circuitry 440 may be one or more general-purpose microprocessors (e.g., any of the PENTIUM microprocessors supplied by Intel Corp.) programmed using any suitable programming language or languages (e.g., C++, C#, java, Visual Basic, LISP, BASIC, PERL, etc.). Suitable control programming is straightforwardly implemented by those of skill in the art without undue experimentation.

In one embodiment, the tool 400 is configured for careful control of the refill process so that the pressure inside the drug reservoir 108 (i.e., the fluid pressure at an outlet of the needle 200) does not exceed a given, critical value. This prevents damage to the pump 100 and also prevents unwanted ejection of drug through the cannula 120 and into the patient. The pressure inside the drug reservoir 108 may be maintained below the critical value in several ways. For example, if liquid is infused into the drug reservoir 108 pneumatically, then the governing circuitry 444 may keep injection pressure below the critical value. A pressure-release valve can also be used in the pneumatic drive as a fail-safe mechanism. As another example, if the liquid is infused using mechanical pumps (e.g., gear, diaphragm, peristaltic, syringe, etc.), the pressure inside the drug reservoir 108 may be controlled by integrating a pressure sensor at the point of highest hydraulic pressure. The governing circuitry 444 may monitor the pressure sensor and employ a conventional feedback system to prevent the pressure at this point from exceeding the critical value. As still another example, the governing circuitry 444 may meter the volume of fluid delivered to the drug reservoir 108 to prevent overfilling. In general, it is only when the reservoir 108 reaches full capacity that the internal pressure begins to rise.

Figure 11:
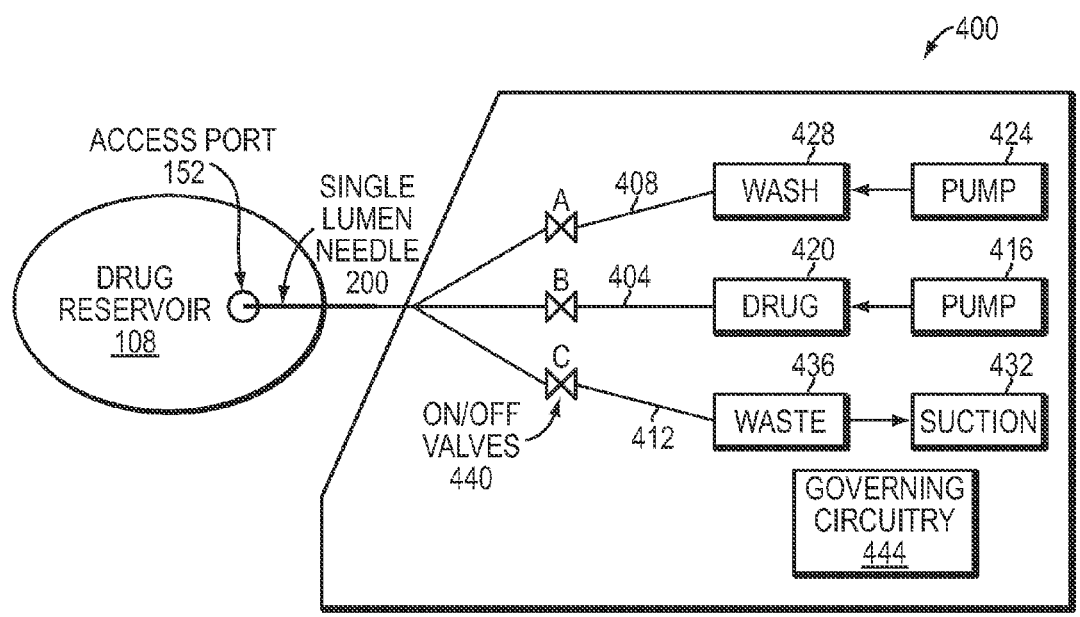
FIG. 11 schematically illustrates a tool, having a single lumen refill needle, inserted into a fill port of an implantable drug-delivery device in accordance with one embodiment of the invention.
Figure 12:
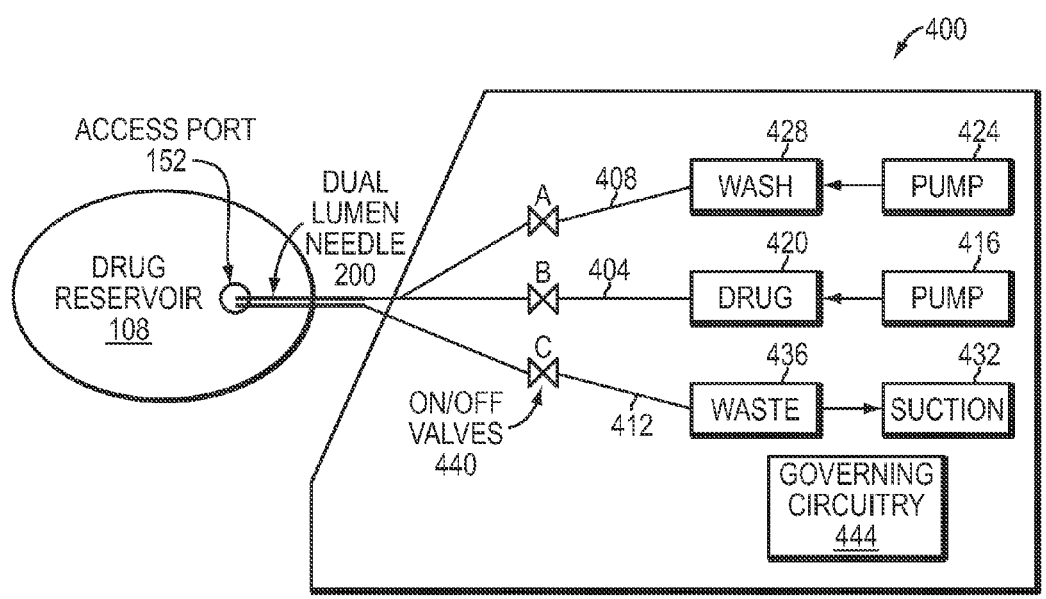
FIG. 12 schematically illustrates a tool, having a double lumen refill needle, inserted into a fill port of an implantable drug-delivery device in accordance with one embodiment of the invention.

For its part, the needle 200 may be a single lumen needle, or the needle 200 may include first and second lumens therethrough. In the case of the single-lumen needle 200, the needle lumen will be in fluid communication with each of the three fluid channels 404, 408, 412, as illustrated in FIG. 11, or, where a separate wash solution 428 and pump 424 therefor are not used, with just each of the first and third channels 404, 412. In the case of the dual-lumen needle 200, the first and second lumens may be fluidly isolated from one another. As illustrated in FIG. 12, the first lumen may be in fluid communication with the first and second channels 404, 408 (or with just the first channel 404 where the separate wash solution 428 and pump 424 therefor are not used) and the second lumen may be in fluid communication with the third channel 412.

Exemplary methods of filling and/or refilling the drug reservoir 108 of the pump 100 may be understood with reference to FIGS. 11 and 12. With reference first to FIG. 11, in this example, the entire refill process is conducted through a single needle 200 (having a single lumen) and a single fill port 152 of the implantable drug-delivery pump 100. All three valves A, B, and C in the valving system 440 are initially closed as the needle 200 is inserted into the fill port 152. As described above with reference to FIGS. 6A-6D, the needle 200 may be advanced into the fill port 152 until its distal tip contacts the stop 220 and its exit port is in fluid communication with the drug chamber or reservoir 108. At that point, the governing circuitry 444 may cause valve C to be opened and any fluid in the reservoir 108 may be removed using suction. In particular, the governing circuitry 444 may cause the vacuum suction pump 432 to apply negative pressure to the third fluid channel 412 so as to aspirate any fluid in the drug reservoir 108 into the waste reservoir 436. The vacuum suction pump 432 may then be shut off and valve C closed by the governing circuitry 444. The circuitry 444 may then cause valve A to be opened and the second pump 424 to apply positive pressure to the second fluid channel 408 so as to drive a wash solution from the wash reservoir 428 through the second channel 408 and the needle 200 lumen into the drug chamber 108. Once sufficient wash solution 428 has been pumped into the drug reservoir 108, the governing circuitry 444 may cause the second pump 424 to be shut off and valve A to be closed. These two steps can be repeated as many times as necessary for effectiveness. Alternatively, during these two steps, valves A and C in the valving system 440 may constantly be kept open, the second pump 424 may continuously pump wash solution into the drug reservoir 108, and the vacuum suction pump 432 may continuously remove fluid from the drug reservoir 108. In this way, the washing and emptying of the drug reservoir 108 occurs in tandem. In still another embodiment, where a separate wash solution 428 and pump 424 therefor are not used (as described above), the drug reservoir 108 of the pump 100 may instead be rinsed, during this purging step, with the drug solution 420. To do so, valve B in the valving system 440 and the first pump 416 are operated by the governing circuitry 444 in a manner similar to that just described for valve A and the second pump 424, respectively.

After the final waste-removal step is complete and the drug chamber 108 has been purged, the governing circuitry 444 may close valves A and C and open valve B to fill the drug reservoir 108 with the drug solution 420. In particular, once valve B is open, the governing circuitry 444 may cause the first pump 416 to apply positive pressure to the first fluid channel 404 so as to drive drug from the reservoir 420, through the first channel 404 and needle 200 lumen, into the drug reservoir 108 of the implanted drug-delivery pump 100. Once a sufficient amount of the drug solution 420 has been pumped into the drug reservoir 108, the governing circuitry 444 may cause the first pump 416 to be shut off and valve B to be closed.

During the entire process described with reference to FIG. 11, the flow rates of the various fluids and the various pressures of injection and suction may all be controlled by the governing circuitry 444. For example, the governing circuitry 444 may monitor or track the pressure in the drug chamber 108, as described above, to prevent it from surpassing a critical value.

With reference now to FIG. 12, in a second example, the entire refill process is conducted through a single needle 200 (having a dual lumen structure) and a single fill port 152 of the implantable drug-delivery pump 100. The two lumens of the needle 200 provide two parallel, isolated paths for fluid to travel in and out of the drug reservoir 108. As indicated in FIG. 12, one of these lumens may be in fluid communication with the third channel 412 and be dedicated to aspiration of fluid from the drug reservoir 108, while the other lumen may be in fluid communication with the first and second channels 404, 408 (or just the first channel 404 where a separate wash solution 428 and pump 424 therefor are not used) and be used to infuse liquid (i.e., drug and/or wash solutions 420, 428) into the drug reservoir 108.

All three valves A, B, and C in the valving system 440 are initially closed as the needle 200 is inserted into the fill port 152. Then, once the needle 200 has been properly inserted, the governing circuitry 444 opens valve C and any fluid in the drug reservoir 108 is removed using suction. The governing circuitry 444 then pumps the drug reservoir 108 full of the wash solution 428 by opening valve A. Again, during this latter step, the suction can either be turned off and multiple suction/wash steps performed (by alternately opening and closing valves A and C), or the suction can be left on to perform a continuous rinse of the drug reservoir 108. In either case, once the final waste-removal step is complete and the drug chamber 108 has been purged, valves A and C may be closed by the governing circuitry 444 and valve B opened to fill the drug reservoir 108 with the drug solution 420.

Once again, the flow rates of the various fluids and the various pressures of injection and suction may all be controlled by the governing circuitry 444, for example to prevent the pressure internal to the drug reservoir 108 from surpassing a critical value. Moreover, as described above, the separate wash solution 428 and pump 424 therefor may be omitted and the drug solution 420 instead used as the wash/rinse solution.

Figure 13:
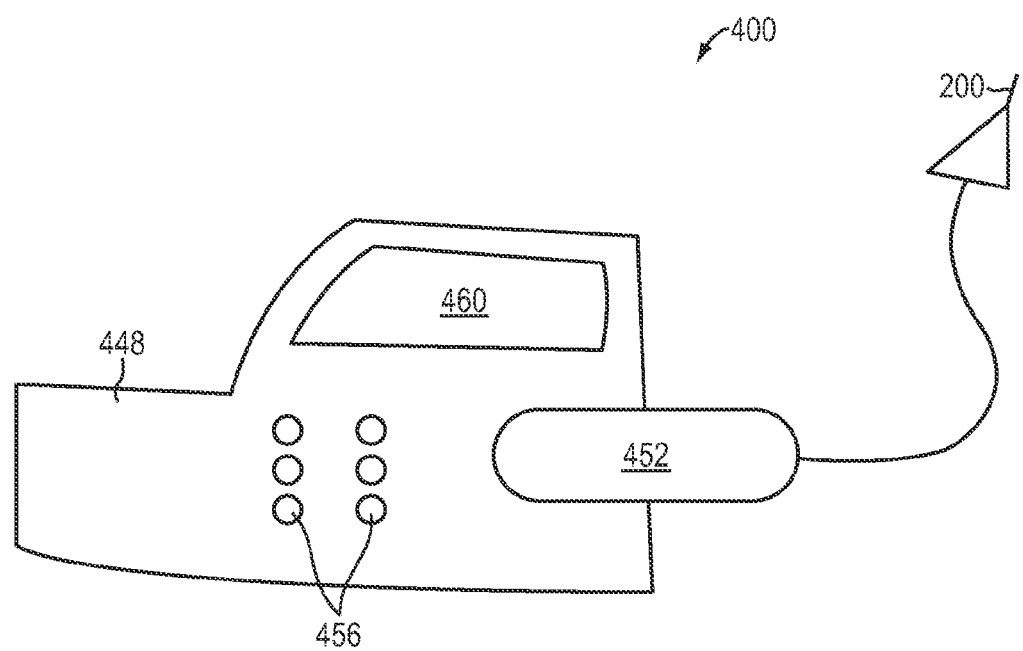
FIG. 13 schematically illustrates the tool of FIG. 10 coupled to an input and display device in accordance with one embodiment of the invention.

FIG. 13 depicts the tool 400 coupled to an input and display device 448 in accordance with one embodiment of the invention. More specifically, a cartridge 452, which may house the pumps 416, 424, 432, the reservoirs 420, 428, 436, the channels 404, 408, 412, and the valving system 440 depicted in FIG. 10, is coupled at one end to the input and display device 448 and at the other end to the needle 200. The governing circuitry 444 is typically part of the input and display device 448, but may in other embodiments be part of the cartridge 452 and interface with the input and display device 448. As illustrated, the input and display device 448 features one or more input buttons 456 and a display screen 460. The display screen 460 may display, for example, the drug and/or the dosage thereof being administered, the cycle at which the tool 400 is at (e.g., emptying, rinsing, filling, standby or ready), the status of the implantable pump 100 (e.g., full, empty), the pressure inside the drug reservoir 108, or any other information of interest to an operator of the tool 400. For their part, the input buttons 456 allow an operator to control the tool 400 (e.g., to select the dosage of the drug to be administered, the mode of operation, the parameters relating to pumping and purging, and the drug to be loaded into the drug reservoir 108), to navigate through various options presented by the display screen 460, etc.

As will be understood by one of ordinary skill in the art, the tool 400 described with reference to FIGS. 10-13 may also be employed to empty, rinse, and/or fill/refill the electrolyte chamber 112. One manner of doing so is to simply replace the drug solution 420 with an appropriate electrolyte solution, and then operate the tool 400 as described above.

Accordingly, as described herein, an operator may rapidly and accurately fill or refill the drug reservoir 108 and/or the electrolyte chamber 112 of the implantable drug-delivery pump 100 in situ via one or more self-sealing, needle-accessible fill ports 152. Moreover, as described, this may be done in a manner that minimizes the risk of damage to the pump 100, and thereby maximizes its effective lifetime.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of filling an implantable drug-delivery pump having a drug chamber, the method comprising the steps of:
    providing a tool comprising:
        (i) first and second independent fluid channels;
        (ii) a fluid reservoir in fluid communication with the first fluid channel; and
        (iii) a needle configured for insertion into a fill port of the implantable drug-delivery pump and having a single lumen in fluid communication with the first and second fluid channels;
    coupling the tool to the fill port of the implantable drug-delivery pump; and
    using the tool to (i) purge the drug chamber and (ii) pump fluid from the fluid reservoir into the drug chamber via the first fluid channel without exceeding a maximum pressure in the drug chamber.

2. The method of claim 1, wherein the purging step comprises pumping fluid from the fluid reservoir into the drug chamber via the first fluid channel and thereafter suctioning the fluid from the drug chamber via the second fluid channel.

3. The method of claim 1, wherein the tool further comprises a third independent fluid channel and a second fluid reservoir in fluid communication therewith, the purging step comprising pumping fluid from the second fluid reservoir into the drug chamber via the third fluid channel and thereafter suctioning the fluid from the drug chamber via the second channel.

4. The method of claim 1, further comprising controlling fluid flow during filling of the implantable drug-delivery pump via opening and closing at least one of first and second valves associated with the first and second independent fluid channels, respectively.

5. A method of filling an implantable drug-delivery pump having a drug chamber, the method comprising the steps of:
    providing a tool comprising:
        (i) first and second independent fluid channels;
        (ii) a fluid reservoir in fluid communication with the first fluid channel; and
        (iii) first and second pumps each fluidly coupled to one of the fluid channels;
    coupling the tool to a fill port of the implantable drug delivery pump; and
    using the tool to:
        (i) apply positive pressure to the first fluid channel so as to drive fluid from the fluid reservoir therethrough;
        (ii) apply negative pressure to the second fluid channel so as to suction the fluid from the drug chamber; and
        (iii) control fluid flow via opening and closing at least one of first and second valves associated with the first and second fluid channels, respectively, so as to prevent fluid pressure at an outlet of the tool from exceeding a predefined level.

6. The method of claim 5, wherein the positive pressure is applied by the first pump and the negative pressure is applied by the second pump.

7. A method of filling an implantable drug-delivery pump having a drug chamber, the method comprising the steps of:

providing a tool comprising:
- (i) first and second independent fluid channels;
- (ii) a fluid reservoir in fluid communication with the first fluid channel; and
- (iii) a needle configured for insertion into a fill port of the implantable drug-delivery pump and having first and second lumens therethrough, the first and second lumens being fluidly isolated from each other and in fluid communication with the first and second fluid channels, respectively;

coupling the tool to the fill port of the implantable drug-delivery pump; and using the tool to (i) purge the drug chamber and (ii) pump fluid from the fluid reservoir into the drug chamber via the first fluid channel without exceeding a maximum pressure in the drug chamber.

8. The method of claim 7, further comprising controlling fluid flow during filling of the implantable drug-delivery pump via opening and closing at least one of first and second valves associated with the first and second independent fluid channels, respectively.

\* \* \* \* \*